United States Patent [19]

Pike

[11] 4,112,950

[45] Sep. 12, 1978

[54] MEDICAL ELECTRONIC APPARATUS AND COMPONENTS

[75] Inventor: Harold L. Pike, Littleton, Colo.

[73] Assignee: Aspen Laboratories, Littleton, Colo.

[21] Appl. No.: 735,097

[22] Filed: Oct. 22, 1976

[51] Int. Cl.² .................... A61B 17/36; A61N 3/02
[52] U.S. Cl. ......................... 128/303.14; 128/303.17; 174/115
[58] Field of Search ............... 128/303.14, 303.17, 128/303.13, 303.15, 303.16, 303.18, 303.19; 174/115

[56] References Cited

U.S. PATENT DOCUMENTS

| 2,110,735 | 3/1938 | Marton | 128/303.18 |
|---|---|---|---|
| 2,180,731 | 11/1939 | Dickinson | 174/115 X |
| 3,275,739 | 9/1966 | Eager, Jr. | 174/115 X |
| 3,502,791 | 3/1970 | Dahlstrom | 174/115 |
| 3,586,751 | 6/1971 | Schoerner | 174/115 |
| 3,602,636 | 8/1971 | Evans | 174/115 |
| 3,720,896 | 3/1973 | Beierlein | 128/303.14 X |
| 3,801,766 | 4/1974 | Morrison, Jr. | 128/303.14 X |
| 3,807,404 | 4/1974 | Weissman et al. | 128/303.14 X |
| 3,816,644 | 6/1974 | Giffel et al. | 174/115 |
| 4,034,761 | 7/1977 | Prater et al. | 128/303.14 |

Primary Examiner—Lee S. Cohen

Attorney, Agent, or Firm—Sheridan, Ross, Fields & McIntosh

[57] ABSTRACT

The apparatus includes a high frequency, high voltage generator, a therapeutic instrument for applying an electric current to a patient, a compound electrical power and control cable connected between the generator and the instrument, and a switch for selectively connecting at least one signal current conductor in the cable to a therapeutic current conductor in the cable to complete a circuit through an activating device for controlling the action of the generator. The cable includes a multiple strand bare therapeutic current conductor wire and preferably two single strand wires with film coatings of low voltage insulation, all of the wires being enclosed in a protective sheath of high voltage insulation. A high voltage is impressed on all of the wires but the voltage differential is very small so that the bare conductor is adequately insulated from the others by the film coatings, with a resulting savings in weight and cost of wire and insulation and improved flexibility. The cable passes into an instrument holder provided with a switch for selectively connecting the signal current conductors to the therapeutic current conductor for control purposes.

6 Claims, 5 Drawing Figures

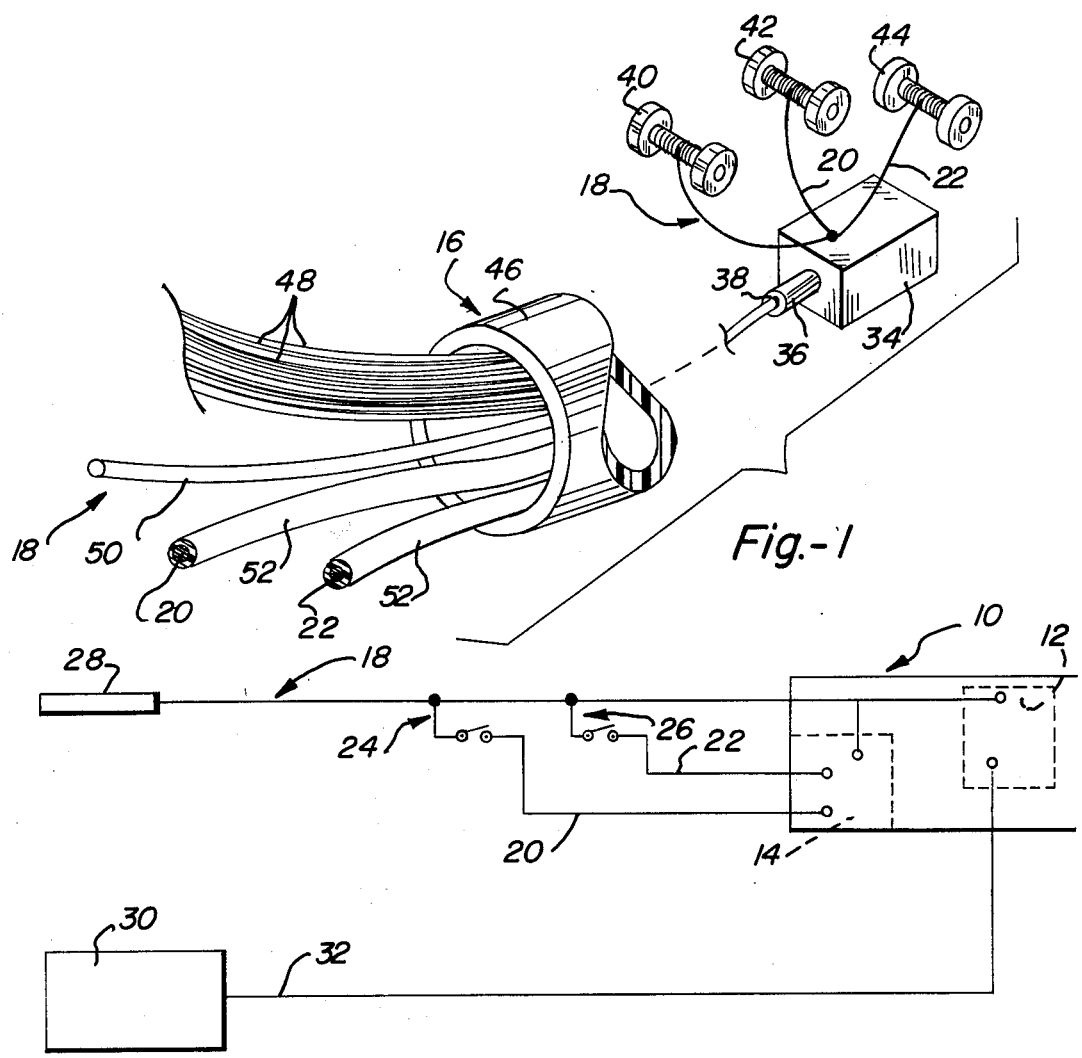
Fig.-1
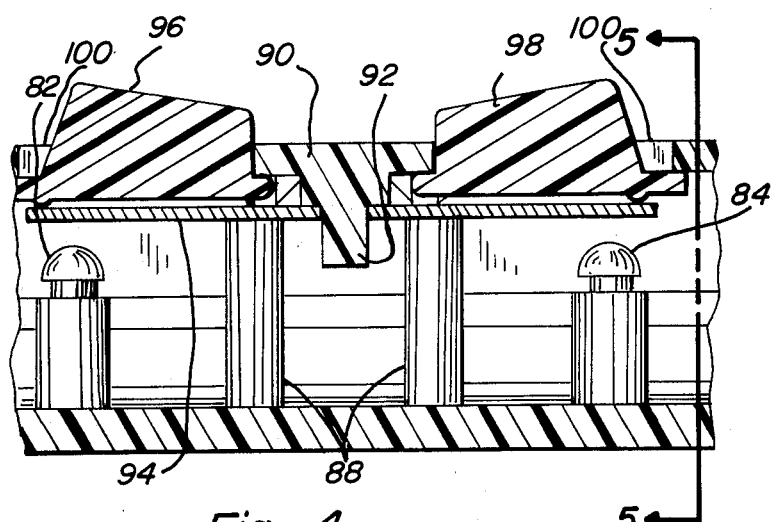
Fig.-2
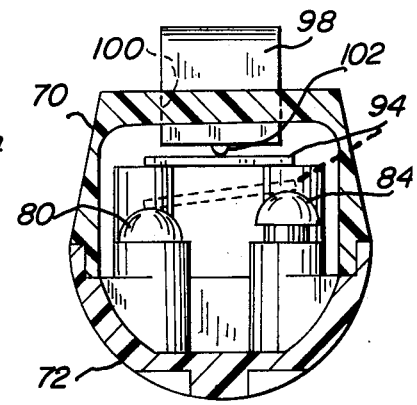
Fig.-4
Fig.-5

MEDICAL ELECTRONIC APPARATUS AND COMPONENTS

BACKGROUND OF THE INVENTION

This invention lies in the field of medical electronic apparatus and is directed to such apparatus which is used for electrosurgical operations. It is more particularly directed to improvements in the conductor cables and switching means which are used in such appliances.

Medical electronic apparatus has been employed for many years for many types of diagnosis and treatment. One field in which there has been considerable growth recently is electrosurgery, in which a suitable generator provides a high frequency, high voltage current which is transmitted to a small surgical electrode having a thin knife-like type to be applied to a patient. The patient sits or lies on a patient plate and is grounded thereto, with the plate being connected by a further conductor back to the generator. The relatively extremely small area of contact by the electrode with the patient provides an intense current in a highly localized area, producing a cutting action. The current passes through the patient's body to the patient plate where the area of contact is so great that no burning effect occurs.

For cutting purposes, the generator is activated to produce a continuous sine wave signal. However, the same instrument may be used to apply to the wound after cutting in order to produce coagulation. For this purpose the generator may be selectively activated to produce a pulsing signal which produces the desired results. Switching means are available for the operator to selectively control an activating means for causing the generator to produce the desired type of current.

Suitable control switches may be mounted on the instrument panel of the generator to be operated by an assistant. The is generally considered to be unsatisfactory because of the delay involved in transmitting instructions. In other designs, foot operated switches are provided which may be controlled by the surgeon. However, this interferes with his mobility because he must stand in one place or move the foot switches about on the floor. Another system which is more desirable consists of a multiple cable conductor extending from the generator to the electrode holder. One conductor is connected to the electrode to carry the therapeutic current and two other conductors are selectively connectable to the therapeutic current conductor through switches to complete circuits back to the activating means for causing the generator to produce the desired mode of current.

While this is the most satisfactory of the three arrangements because the surgeon is free to move about and has instant control of the current modes, there are still various disadvantages in the devices previously available. The electrode holders and switches are larger and heavier than need be, and the compound cables are heavier and stiffer than necessary so that the use of these devices is annoying and tiring to the surgeon. The usual compound cable makes use of three multiple strand conductors, each encased in high voltage insulation, with the three conductors further encased in a sheath of high voltage insulation. Such cable is relatively stiff and heavy and also expensive. Since all of the components are rather expensive it is necessary to use them repeatedly and this adds the further difficulty and expense of sterilization before each use.

SUMMARY OF THE INVENTION

The construction of the present invention overcomes the difficulties mentioned above and provides a device which is extremely light and easy to use and which is so inexpensive that it is possible to obtain it in sterile condition, use it once and discard it without any need for re-sterilization and re-use.

The compound cable includes a first therapeutic current conductor component comprising a length of multiple strand bare conductor wire and two signal current conductor components each comprising a length of single strand conductor wire provided with a film coating of low voltage insulating material. The components are arranged in contacting parallel juxtaposition, and a protective sheath of high voltage insulating material surrounds the components and maintains them in proper relation.

The therapeutic current conductor carries a current at a very high voltage, which may be 4,000 volts or higher, for performing the surgical work. The circuit which includes the signal current conductors, the therapeutic current conductor, and the activating means operates at a voltage which differs by only a slight amount from that of the therapeutic current conductor. The difference is only about 10 volts and need not be more than 15 volts. Thus, the film coating, which has an insulating value of about 50 to 100 volts, is adequate to prevent shorting between the conductors, and there is no need for any individual insulation on the bare wire. Of course, the two single strand conductors operate at substantially the same voltage. The protective sheath prevents shorting to any external objects and therefore has an insulating value higher than the operating voltage, the value being at least about 5,000 volts.

The multiple strand wire is large enough to carry the therapeutic current. The single strand wires carry only a very small current and thus may be very light gauge for this purpose. The minimum gauge is determined primarily by the strength necessary to resist mechanical stresses such as bending. At the present time 30 gauge wire is being used successfully.

The great reduction in the weight and cost of the amount of wire and insulation used in this cable makes it so inexpensive that it is possible to discard it after a single use. The reduced weight and the increased flexibility also facilitate the work of the surgeon.

The electrode holder is a slender elongate hollow casing of rigid plastic material only slightly larger than a pencil, with axial openings at each end. The compound cable enters at a first end and extends throughout a major portion of the length of the casing, the therapeutic current conductor being connected at its forward to a socket for receiving the shank of the surgical electrode. It is also connected to a pair of longitudinally spaced electrical contacts located at one side of the center line of the casing. Another pair of similarly spaced electrical contacts are located at the other side of the center line and each signal current conductor is connected to one of them.

A thin elongate resilient strip of conductive metal is fixed at its mid portion above the sets of contacts, with one end portion overlying the two forward contacts and the other end portion overlying the two aft contacts. Actuator buttons are movably mounted in the casing above the two ends and may be selectively operated by the surgeon to depress either end of the strip into engagement with its respective contacts and send a signal to the activating device for the desired mode.

BRIEF DESCRIPTION OF THE DRAWINGS

Various other advantages and features of novelty will become apparent as the description proceeds in conjunction with the accompanying drawings, in which:

FIG. 1 is a diagrammatic perspective view showing a conventional extrusion coating apparatus and a greatly enlarged portion of the novel compound cable;

FIG. 2 is a schematic block diagram illustrating the arrangement and connection of the various parts of the total apparatus;

FIG. 4 is a sectional view taken on line 4—4 of FIG. 3; and

FIG. 5 is a sectional view taken on line 5—5 of FIG. 4.

DESCRIPTION OF PREFERRED EMBODIMENTS

Figure 3:
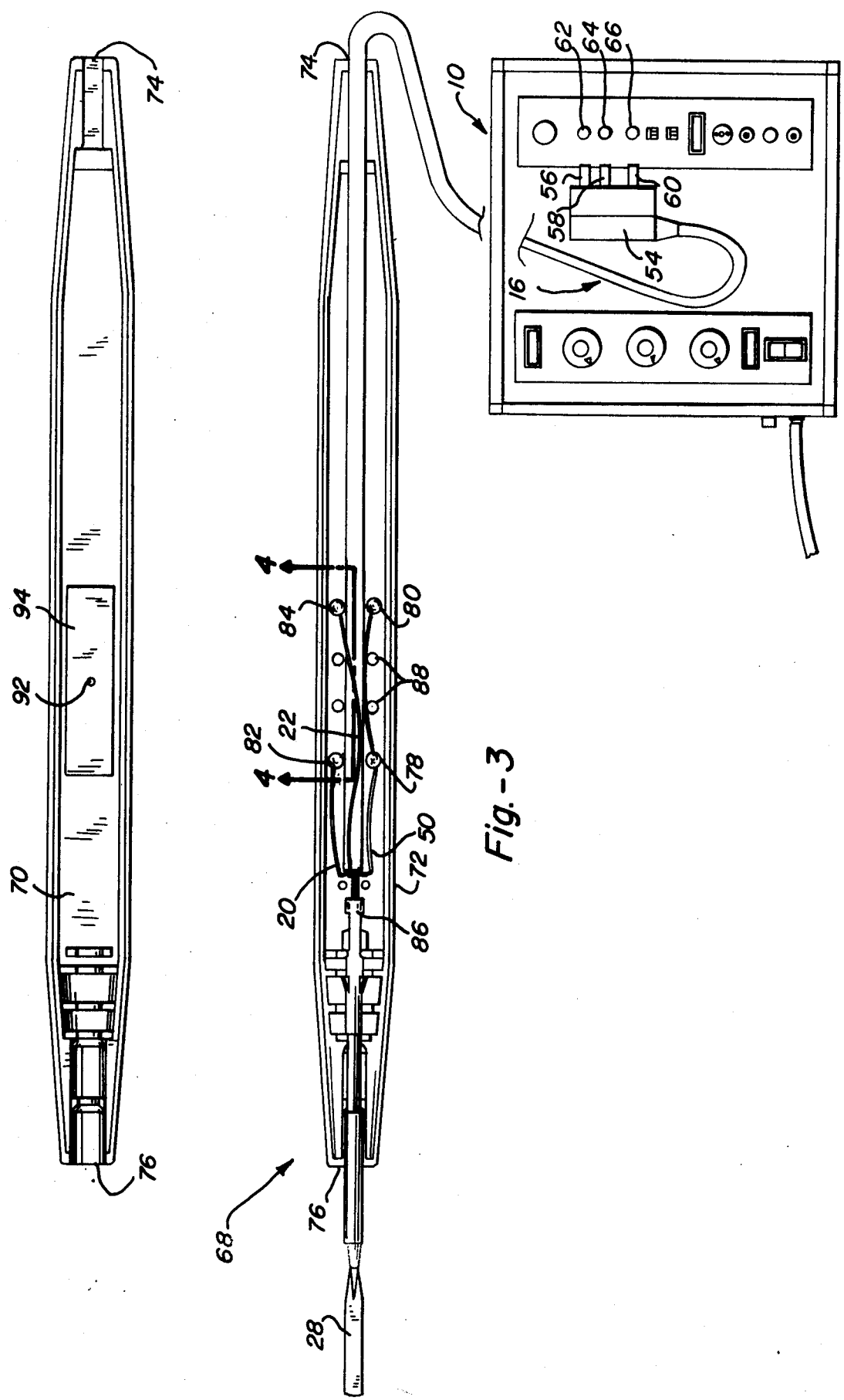
FIG. 3 is an exploded view showing the construction of the casing and switch means.

The general arrangement of a total apparatus incorporating the features of the invention is diagrammatically illustrated in FIG. 2, in which the power unit housing 10 encloses a suitable high frequency high voltage generator 12 and an activating means 14 for controlling the action of the generator and causing it to produce a continuous sine wave signal for cutting purposes or a pulsating signal for coagulating purposes.

The compound electrical power and control cable 16 of FIGS. 1 and 3 is illustrated in FIG. 2 as comprising a first therapeutic current conductor component 18 and second signal current conductor components 20 and 22. Switches 24 and 26 are selectively operable to connect either component 20 or component 22 to component 18 to complete a signal circuit through the activating means 14, which in turn causes the generator 12 to produce the desired mode of current. Component 18 is connected to the surgical electrode 28, and the patient plate 30 is connected by conductor 32 back to the generator.

As seen in FIG. 1, a conventional extrusion coating apparatus 34 is provided with an extrusion die 36 having an orifice 38. Reels 40, 42 and 44 carry respectively supplies of conductor components 18, 20 and 22, and each of these components is fed into the interior of apparatus 34, which contains a bath of high voltage plastic coating material and pumping apparatus to pressurize the bath. Within the apparatus the three components are combined in adjacent parallelism and passed as a unit centrally out of die 36. The high voltage plastic insulating material is forced out of the die by the pumping means around the combined lengths of material to form a protective sheath 46 which surrounds the components and maintains them in assembled relation. The sheath may be polyvinyl chloride or other suitable flexible plastic material.

It will be seen that conductor component 18 is made up of a plurality of light gauge wires 48, which are preferably about 36 gauge, and one heavier gauge wire 50, which is preferably about 30 gauge. All of these wires are bare. Conductor components 20 and 22 are single strand wires, also of about 30 gauge, and are provided with a film coating 52 of epoxy resin or the like which may have an insulating value of 50 to 100 volts. Sheath 46 has an insulating value of at least about 5000 volts. The working voltage in the example for the therapeutic current conductor may be about 4000 volts. In such case the voltage for the signal current conductors will be about 4005 to 4010 volts. Thus, the differential voltage is only about 10 volts, and the film coating is adequate to prevent shorting between any of the conductors. With any working voltage the sheath is made adequate to prevent shorting to any external object.

Turning to FIG. 3, compound cable 16 is connected to plug 54 provided with prongs 56, 58 and 60 connected to conductor components 18, 20 and 22, and the prongs are engageable with sockets 62, 64, 66 in power unit housing 10 to complete the circuitry illustrated in FIG. 2.

The electrode holder 68, shown in open condition in FIG. 3, comprises upper and lower halves 70 and 72 which are combined to form a pencil-like slender, elongate, hollow casing having an axial opening 74 at a first end and an axial opening 76 at its second end. A first pair of electrical contacts 78, 80 are located in the casing in longitudinally spaced relation at one side of the center line and a second pair of electrical contacts 82, 84 are located in the casing at the other side of the center line with the same longitudinal spacing and in lateral registry with the first pair.

The sheath 46 terminates shortly forward of the contacts and the heavier gauge wire 50 of the multiple strand conductor 18 is separated from the smaller wires, bent back, and anchored under contacts 78 and 80 to form a common connection. The insulation is removed from the end portions of each of the single strand conductors 20 and 22 and one of them is anchored under each of the contacts 82 and 84. Since all of these wires are of the same gauge the tops of all four contacts will be at the same level. The smaller gauge wires 48 of conductor 18 are brought forward and connected to socket 86 which is adapted to receive the shank of electrode 28.

Four small support posts 88, two at each side of the center line extend upward between the contacts to a level above the upper ends of the contacts. As can be seen in FIG. 4, a boss 90 is formed in the under side of upper half 70 and includes a central locating pin 92. A longitudinally arranged elongate resilient strip 94 of conductive metal such as copper or brass is formed with a small aperture which fits on pin 92. When the casing halves are brought together the strip is gripped between boss 90 and support posts 88 and anchored against longitudinal movement by pin 92, and in its unflexed condition is located in spaced relation above the contacts with one end overlying contacts 80 and 84 and with the other end overlying contacts 78 and 82.

Two actuator buttons 96 and 98, flanged around their lower margins, are mounted for free movement in apertures 100, their lower sides contacting the ends of the strip and their upper portions extending to the exterior of casing 68. When button 96 is pressed down it deflects the forward end portion of the strip into engagement with contacts 78 and 82 and completes a circuit back to the activating means 14 to cause the generator to produce a therapeutic current in one desired mode. When button 98 is pressed down it deflects the aft end portion of the strip into engagement with contacts 80 and 84 and completes a different circuit back to the activating means to cause the generator to produce a therapeutic current in another desired mode.

The wire 50 is heavier than wires 48 so that it will have adequate strength to resist the forces applied in bending it back and wrapping it under the contacts. It is of the same gauge as wires 20 and 22 so that when they are all wrapped under the contact heads and the latter are pressed into their mountings the upper surfaces of the contacts will all be at the same level for proper engagement by strip 94. However, slight inaccuracies in manufacture will occasionally cause one contact to be slightly higher than the other as illustrated in exaggerated form in FIG. 5. If strip 94 were pressed down in perfectly flat form it would engage only contact 84 and the circuit would not be completed. To forestall this difficulty each button is formed with a small projection 102 on its lower face substantially midway between its sides. When the button is depressed the projection will contact a central area of the end portion of the strip, twisting it about contact 84 as a fulcrum and forcing the opposite marginal portion down into engagement with contact 80 as shown in broken lines.

The invention has been described in detail with particular reference to preferred embodiments thereof, but it will be understood that variations and modifications can be effected within the spirit and scope of the invention.

What is claimed is:

1. Medical electronic apparatus comprising:
   a generator for producing high frequency, high voltage current;
   a therapeutic instrument including an electrode for applying the generated current to a patient;
   and a compound electrical power and control cable connected to the generator, therapeutic instrument and electrode:
   the cable including a first therapeutic current conductor component comprising a length of multiple strand bare conductor wire, including one strand of substantially heavier gauge than the other strands, and at least one second signal current conductor component comprising a length of single strand conductor wire provided with a film coating of low voltage insulating material;
   the components being arranged in contacting parallel juxtaposition;
   and a protective sheath of high voltage insulating material surrounding the components;
   both components carrying current at high voltage with a relatively small voltage differential between them;
   and switch means connected between the heavier gauge bare wire and the signal current conductor component wire to selectively connect the components electrically;
   the film coating on the signal current conductor component wire having a higher insulating value than the voltage differential between the components;
   and the protective sheath having a higher insulating value than the voltage applied to either the therapeutic current conductor component or the signal current conductor component.

2. Apparatus as claimed in claim 1, further including:
   a plurality of signal current conductor component insulated wires;
   said switch means including separate switch means for selectively connecting each signal current conductor component wire to the heavier gauge bare wire, the voltage applied to each signal current conductor component wire being of substantially the same value.

3. A compound electrical power and control cable for use in combination with medical electronic apparatus, comprising:
   a first conductor component comprising a length of multiple strand bare conductor wire, including one strand of substantially heavier gauge than the other strands;
   at least one second conductor comprising a length of single strand conductor wire provided with a film coating of low voltage insulating material;
   the components being arranged in contacting parallel juxtaposition; and
   a protective sheath of high voltage insulating material surrounding the components and maintaining them in juxtaposed relation.

4. A cable as claimed in claim 3, in which at least two second conductor components of single strand film insulated wire are provided.

5. A cable as claimed in claim 3, in which the heavier gauge bare wire is of approximately the same gauge as the film insulated wires.

6. A cable as claimed in claim 3, in which the film coating has an insulating value of about 50 to 100 volts and the protective sheath has an insulating value of at last about 5000 volts.

* * * * *

UNITED STATES PATENT AND TRADEMARK OFFICE
CERTIFICATE OF CORRECTION

PATENT NO. : 4,112,950
DATED : September 12, 1978
INVENTOR(S) : HAROLD L. PIKE

It is certified that error appears in the above–identified patent and that said Letters Patent are hereby corrected as shown below:

Column 6, line 31, after "conductor" insert --component--.

Signed and Sealed this

Nineteenth Day of December 1978

[SEAL]

Attest:

RUTH C. MASON
Attesting Officer

DONALD W. BANNER
Commissioner of Patents and Trademarks